United States Patent [19]

Wagner et al.

[11] Patent Number: 5,306,309
[45] Date of Patent: Apr. 26, 1994

[54] SPINAL DISK IMPLANT AND IMPLANTATION KIT

[75] Inventors: William R. Wagner; Richard L. Lariviere, both of Escondido; Scott D. Slabbekoorn, Vista, all of Calif.

[73] Assignee: Calcitek, Inc., Carlsbad, Calif.

[21] Appl. No.: 878,196

[22] Filed: May 4, 1992

[51] Int. Cl.$^5$ ............................................. A61F 2/44
[52] U.S. Cl. ....................................... 623/17; 606/61
[58] Field of Search ..................... 623/17, 16; 606/53, 606/60, 61

[56] References Cited

U.S. PATENT DOCUMENTS

| | | | |
|---|---|---|---|
| 2,677,369 | 5/1954 | Knowles | 623/17 |
| 3,848,601 | 11/1974 | Ma et al. | 128/305 |
| 4,309,777 | 1/1982 | Patil | 623/17 |
| 4,349,921 | 9/1982 | Kuntz | 623/17 |
| 4,714,469 | 12/1987 | Kenna | 623/17 |
| 4,743,256 | 5/1988 | Brantigan | 623/17 |
| 4,743,256 | 5/1988 | Brantigan | 623/17 |
| 4,759,766 | 7/1988 | Buettner-Janz et al. | 623/17 |
| 4,759,769 | 7/1988 | Hedman et al. | 623/17 |
| 4,772,287 | 9/1988 | Ray et al. | 623/17 |

(List continued on next page.)

FOREIGN PATENT DOCUMENTS

| | | |
|---|---|---|
| 89/02791 | 1/1990 | PCT Int'l Appl. |
| 9000037 | 1/1990 | PCT Int'l Appl. |
| 90/00819 | 5/1991 | PCT Int'l Appl. |

OTHER PUBLICATIONS

John Frymoyer et al., "The Adult Spine", Raven Press, pp. 1167–1170 (1991).

T. Koyama et al., "Porous Hydroxyapatite Ceramics for Use in Neurosurgical Practice", Surg. Neurol., vol. 25, pp. 71–73 (1986).

Stephen D. Cook et al., "Evaluation of Hydroxylapatite Graft Materials in Canine Cervical Spine Fusions", Spine, vol. 11, No. 4, pp. 305–309 (1986).

Howard Senter et al., "Anterior Cervical Discectomy with Hydroxylapatite Fusion", Neurosurgery, vol. 25, No. 1, pp. 39–43 (1989).

G. Lozes et al., "Discectomies of the Lower Cervical Spine Using Interbody Biopolymer (B.O.P.) Implants", Acta Neurochirurgica, vol. 96, pp. 88–93 (1989).

M. Jarcho, "Calcium Phosphate Ceramics as Hard Tissue Prosthetics", Clinical Orthopaedics, vol. 157, pp. 259–278 (1981).

M. Jarcho, "Biomaterial Aspects of Calcium Phosphates", Dental Clincs of North America, vol. 30, No. 1, pp. 25–47 (1986).

M. Block et al., "Loaded Hydroxylapatite Coated and Grit-Blasted Titanium Dental Implants in Dogs", Int'l.

(List continued on next page.)

Primary Examiner—Randall L. Green
Assistant Examiner—Dinh X. Nguyen
Attorney, Agent, or Firm—Gregory Garmong; Donald R. Greene; Saul Leitner

[57] ABSTRACT

A spinal disk implant comprises a solid body having four faces arranged to define a right-rectangular solid body and two faces that define the ends of the solid body. The faces that define the right-rectangular body include two opposed side faces and two opposed transverse faces. The transverse faces have a central region with three-dimensional features thereon and an anterior platform region lying along an anterior margin of the transverse faces. The faces defining the ends of the solid body include a convexly curved anterior face and a posterior face. The solid body is made of a biocompatible synthetic material. A kit that may be used by a surgeon includes an implant and an implant delivery tool dimensioned to releasably hold the implant. The delivery tool preferably has a pair of flexible opposed arms extending from a base, separated so that the implant can fit between the arms, and may have a breakable release band extending around the implant to hold it in place until a weak link in the release band is intentionally broken during implantation.

33 Claims, 3 Drawing Sheets

U.S. PATENT DOCUMENTS

| | | | |
|---|---|---|---|
| 4,834,757 | 5/1989 | Brantigan | 623/17 |
| 4,863,476 | 9/1989 | Shepperd | 623/17 |
| 4,863,477 | 9/1989 | Monson | 623/17 |
| 4,874,389 | 10/1989 | Downey | 623/17 |
| 4,878,915 | 11/1989 | Brantigan | 623/17 |
| 4,904,260 | 2/1990 | Ray et al. | 623/17 |
| 4,904,261 | 2/1990 | Dove et al. | 623/17 |
| 4,911,718 | 3/1990 | Lee et al. | 623/17 |
| 4,917,704 | 4/1990 | Frey et al. | 623/17 |
| 4,932,969 | 6/1990 | Frey et al. | 623/17 |
| 4,932,975 | 6/1990 | Main et al. | 623/17 |
| 4,936,848 | 6/1990 | Bagby | 623/17 |
| 4,946,378 | 8/1990 | Hirayama et al. | 623/17 |
| 4,955,908 | 9/1990 | Frey et al. | 623/17 |
| 4,997,432 | 5/1991 | Keller | 623/17 |
| 5,002,576 | 5/1991 | Fuhrman et al. | 623/17 |
| 5,015,247 | 5/1991 | Michelson | 606/61 |

OTHER PUBLICATIONS

*J. Oral Maxillofac. Implants,* vol. 4(3), pp. 219–225 (1989).

Stephen D. Cook et al., "Hydroxylapatite-Coated Titanium for Orthopedic Implant Applications", *Clinical Orthopedics and Related Research,* No. 232, pp. 225–243 (1988).

T. Yamamuro et al., "Replacement of the Lumbar Vertebrae of Sheep with Ceramic Prostheses", *The Journal of Bone and Joint Surgery,* vol. 72–B, pp. 889–893 (1990).

P. Ylinen et al., "Lumbar spine interbody fusion with reinforced hydroxyapatite implants", *Arch. Orthop. Trauma. Surg.,* vol. 110, pp. 250–256 (1991).

Marbin Bloom et al., "Anterior Intervertebral Fusion of the Cervical Spine", *J. Bone and Joint Surgery,* vol. 63(5), p. 842 (1981).

SPINAL DISK IMPLANT AND IMPLANTATION KIT

BACKGROUND OF THE INVENTION

This invention relates to implants surgically placed into the human body and the tool used to perform the implantation, and, more particularly, to an implant placed between two vertebrae to fuse them together and its implant delivery tool.

The human spine is composed of a column of 33 bones, termed vertebrae, and their joining structures. The 24 vertebrae nearest the head, collectively termed the presaccral vertebrae, are separate bones capable of individual movement. The bodies of the presaccral vertebrae are generally connected by anterior and posterior longitudinal ligaments and by discs of fibrocartilage, termed intervertebral disks, positioned between opposing faces of adjacent vertebral bodies. These mobile vertebrae may be classified by their position and function into either cervical, thoracic, or lumbar vertebrae. The remaining 9 vertebrae are fused to form the saccrum (5 vertebrae) and the coccyx (4 vertebrae) and are incapable of individual movement.

This column of vertebrae and intervertebral disks forms a central axis for supporting the load of the head and torso. The vertebral body and the dorsal vertebral arch of each of the 24 mobile presaccral vertebrae enclose an opening, termed the vertebral for amen, through which the spinal cord, a column of nerve tissue which communicates nerve impulses between the brain and the rest of the body, and the spinal nerve roots pass and are protected from damage.

The presaccral vertebrae are normally held in a precise relation to each other by the intervertebral disks, the longitudinal ligaments, and the musculature of the body. These vertebrae can move relative to adjacent vertebrae in various manners, permitting the head to be turned relative to the body and providing a wide range of flexibility to the spine. The movement between individual pairs of vertebrae is limited to prevent local pressure on the spinal cord or excessive bending of the spinal cord. Such pressure or bending could possibly result in disorders associated with blockage of the nerve impulses traveling along the spinal cord, in turn producing pain, paresthesia, or loss of motor control which must be resolved by removing the causative condition.

The nerve conduction disorders may also be associated with the intervertebral disks or the bones themselves. One such condition is a herniation of the intervertebral disk, in which a small amount of tissue protrudes from the sides of the disk into the foramen to compress the spinal cord. A second common condition involves the development of small bone spurs, termed osteophytes, along the posterior surface of the vertebral body, again impinging on the spinal cord.

Upon identification of the abnormality causing the conduction disorders, surgery may be required to correct the problem if more conservative treatment fails. For those problems associated with the formation of osteophytes or herniations of the intervertebral disk, one such surgical procedure is intervertebral discectomy. In this procedure, the involved vertebral bodies are exposed and the intervertebral disk is removed, thus removing the offending tissue, or providing access for the removal of the bone osteophytes. A second procedure, termed a spinal fusion, may then be required to fix the vertebral bodies together to prevent movement and maintain the space originally occupied by the intervertebral disk. Although there may result some minor loss of flexibility in the spine, because of the large number of vertebrae, the loss of mobility is usually acceptable.

During a spinal fusion following a discectomy, an implant is inserted into the intervertebral space. This intervertebral implant is often a bone graft removed from another portion of the patient's body, termed an autograft. The use of bone taken from the patient's body has the important advantage of avoiding rejection of the implant, but has some shortcomings. There is always a risk in opening a second surgical site for obtaining the bone graft, which can lead to infection or pain for the patient, and the site of the bone graft is weakened by the removal of bony material. The bone implant may not be perfectly shaped and placed, leading to slippage or absorption of the implant, or failure of the implant to fuse with the vertebrae.

Other options for a graft source for the implant are bone removed from cadavers, termed an allograft, or from another species, termed a xenograft. In these cases, while there is the benefit of not having a second surgical site as a possible source of infection or pain, there is the increased difficulty with graft rejection and the risk of transmitting communicable diseases.

An alternative approach to using a bone graft is to use a manufactured implant made of a synthetic material that is biologically compatible with the body and the vertebrae. Several compositions and geometries of such implants have been utilized, ranging from simple blocks of material to carefully shaped implants, with varying success. No fully satisfactory implant has been reported. In some instances, the implanting surgery is readily accomplished, but the results are unsatisfactory due to side effects or dislocation of the implant. In other instances, the implant requires a complex surgical procedure that is difficult to perform and still may not lead to correction of the problem for the reasons indicated.

There is therefore a need for an improved spinal disk implant, which is both readily utilized ln a surgical procedure and has a high probability of success without undesirable side effects. The present invention fulfills this need, and further provides related advantages.

SUMMARY OF THE INVENTION

The present invention provides a readily manufactured and implanted spinal disk implant. The disk implant is configured to engage the cortical bone region of the vertebrae after implantation, so that the majority of the loading transmitted through the implant is carried by the cortical bone. Since the cortical bone is harder than the cancellous bone region of the vertebrae, it is less likely that the spinal column will post-operatively compress around the implant. The implant also provides structure to improve the engagement between the implant and the adjacent vertebrae, minimizing the likelihood that there will be post-operative slippage of the implant from its proper intervertebral position. The implant is made of an artificial material that can be fully sterilized prior to implantation.

The invention also includes a disk implantation kit containing an implant and a delivery tool useful in performing the intervertebral placement of the implant during a surgical procedure. The disk implant may be provided in a presterilized, prepackaged form held by the delivery tool, which can be used without repositioning the implant in the tool. The implantation tool carries the implant so as to avoid damage to the implant prior to and during surgical implantation. The tool also permits the surgeon to securely hold the implant during implantation and to easily place it at the proper location.

In accordance with the invention, a spinal disk implant comprises a solid body having four faces arranged to define a right-rectangular body, including two opposed side faces and two opposed transverse faces. At least one of the transverse faces is provided with a central region with three-dimensional features thereon and an anterior platform region lying along an anterior margin of the transverse face. A convexly curved anterior face defines one end of the right-rectangular body, and a posterior face defines the other end of the right-rectangular body. The solid body is made of a material selected from the group consisting of a ceramic, a metal, a polymer, and a composite material.

Stated more formally, the spinal disk implant is a solid body made of a biocompatible synthetic material and has a convexly (outwardly) curved anterior face with a curvature of about that of the anterior surface of a human vertebra. The anterior face has an anterior face lateral margin and a curved anterior face transverse margin.

The disk implant also has a posterior face spaced apart from the anterior face with a posterior face lateral margin and a posterior face transverse margin. The posterior face may be flat or convexly curved.

A pair of generally parallel, spaced apart, opposed side faces extend between the lateral margins of the anterior face and the posterior face.

A pair of spaced apart, opposed transverse faces extend between the transverse margins of the anterior face and the posterior face. The transverse faces may be flat or convexly curved. The transverse faces may be parallel or angled toward each other. Each transverse face has an anterior platform. At least one of the transverse faces, and preferably both transverse faces, has an engagement region located posterior of the anterior platform with three-dimensional features thereon. The width of the anterior platform is about that of the thickness of anterior cortical bone of a human vertebra.

In a preferred form, the implant is made available to surgeons in a kit prepackaged with a delivery tool comprising means for holding the implant and then controllably releasing the implant. The delivery tool preferably includes a base and a pair of flexible opposed arms extending from the base. The arms are spaced and dimensioned to releasably hold the implant there between. A release band, preferably (but not necessarily) extending between the distal ends of the arms, holds the implant to the delivery tool. The release band has a breakable weak link, which is readily parted with a slight tug after the implant has been properly positioned by the surgeon. This configuration of delivery tool avoids the need for threaded bores or other types of grasping features on the implant, as these types of features may significantly weaken the implant. A delivery tool handle is also provided so that the tool can be easily manipulated by the surgeon.

In the preferred kit form, the delivery tool is made of a sterilizable plastic. The kit is provided with the implant grasped between the arms of the delivery tool, in a presterilized package. The implants are provided in a range of sizes for different size persons and different locations of the disk to be replaced. The surgeon makes a preoperative estimation of the range of sizes most likely to be required, and delivery tool/implant sets spanning this range are prepared for surgery. During the implant procedure, the surgeon can select the one implant that is most appropriate, and substitute another if for some reason, typically incorrect dimensions, the first choice is not operable. The surgeon need not modify the shape of the implant, but uses it directly from the package. The implant is placed into the correct position using the delivery tool, the implant is controllably released, and the delivery tool is removed and discarded. This approach minimizes the time of the operation, thereby decreasing the chances of complications for the patient.

The present invention provides an important advance in the art of spinal disk implants. The implant itself is configured to provide the most reliable and secure load path through the reconstructed region, and also to securely hold its position post-operatively. The delivery tool encourages the proper placement of the implant during surgery, and also aids in achieving orderly functioning of the operating theater with reduced risk of patient complications. Other features and advantages of the invention will be apparent from the following more detailed description of the preferred embodiments, taken in conjunction with the accompanying drawings, which illustrate, by way of example, the principles of the invention.

DETAILED DESCRIPTION OF THE PREFERRED EMBODIMENTS

Figure 1:
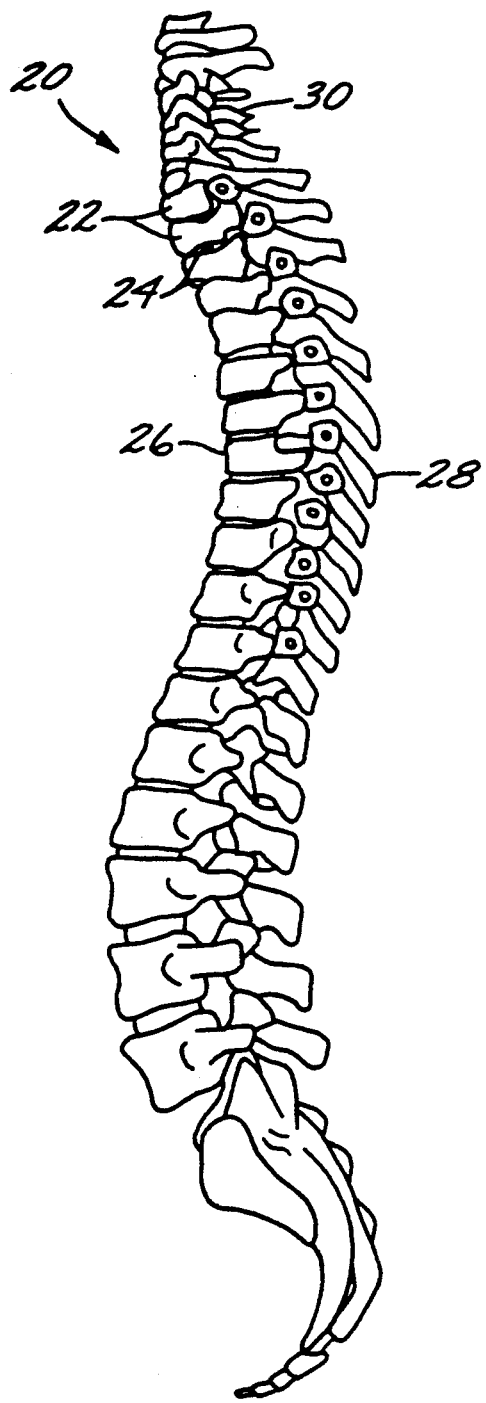
FIG. 1 is a side elevational view of the spine.

FIG. 1 depicts a human spine 20. The spine 20 is formed from thirty-three individual vertebrae. 22, with the twenty-four uppermost vertebrae in most cases separated by intervertebral disks 24. The spine 20 is described as having an anterior side 26 and a posterior side 28.

Figure 2:
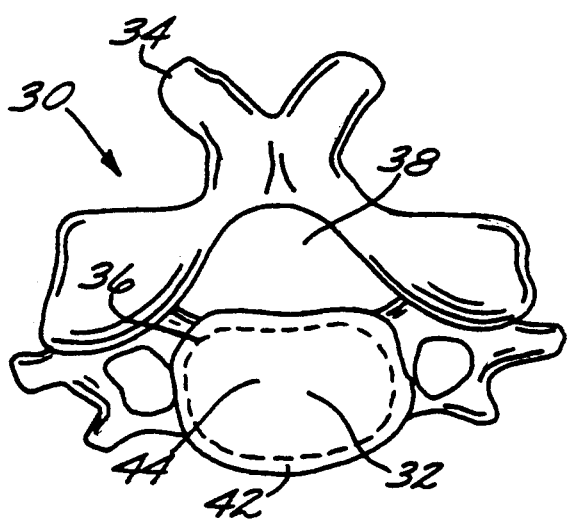
FIG. 2 is an enlarged plan view of a cervical vertebra.

FIG. 2 depicts one of the vertebrae, here one of the cervical vertebrae 30. (A cervical vertebra has been chosen for illustration, but the other vertebra are similar in relevant aspects and differ primarily in details of geometry.) The vertebra 30 includes a vertebral body region 32, and various processes 34. A cervical disk 36, indicated in phantom lines, overlies the vertebral body region 32 in the natural condition. A central opening through the vertebra 30 is the foramen 38, through which the spinal cord and the spinal nerve roots pass.

The vertebral body region 32 includes two distinct types of natural bone. A layer of cortical bone is found at an outer edge 42 of the vertebral body region 32. The cortical bone is a hard, dense type of bone, having high strength. A central portion 44 of the vertebral body region 32 is made of cancellous bone, which is a more resilient, weaker, and less dense type of bone.

A spinal disk implant 50, shown in FIGS. 3-7 in several variations, has a structure designed for implantation between the vertebral body regions of two adjacent vertebrae 22. This spinal disk implant 50 is readily inserted between the vertebrae during a surgical procedure, produces a load-bearing joint in which the majority of the load on the spine 20 is borne through the cortical bone, and is highly resistant to dislocation away from its proper position between the vertebrae.

Figure 3:
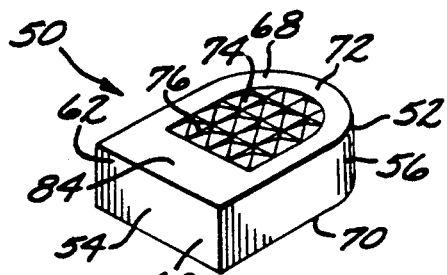
FIG. 3 is a perspective view of a first embodiment of a spinal disk implant.
Figure 4:
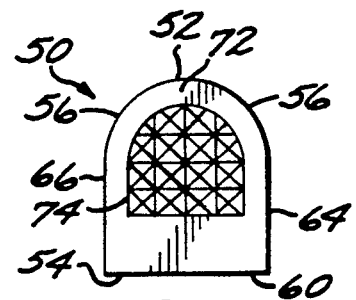
FIG. 4 is a plan view of the spinal disk implant of FIG. 3.
Figure 5:
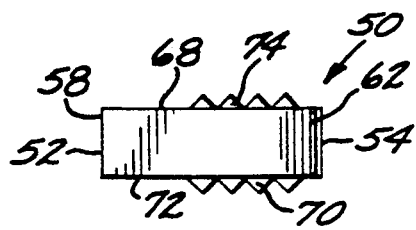
FIG. 5 is a side elevational view of one form of the spinal disk implant of FIG. 3.

Referring to FIGS. 3-5, the spinal disk implant 50 is a solid body having an anterior face 52 and an oppositely disposed posterior face 54. The anterior face 52 of the implant 50 is convexly curved, to generally match the shape of the anterior portion of the outer edge 42 of the vertebra 22 (FIG. 2). As discussed herein, several features of the implant are configured to be approximately the same shape or dimension as features of the vertebrae. It is recognized that different persons and different vertebrae have differing shapes and dimensions, and the implant features are selected to be close, but not necessarily exact, matches for those shapes and dimensions. As discussed subsequently, the implant may be made available to surgeons in a range of sizes to accommodate extremes and normal shapes and dimensions that are encountered in different persons.

The anterior face 52 has an anterior face lateral margin 56 and an anterior face transverse margin 58. The term "margin" 18 used herein generally in the same sense as in the "margin" of a page, its edge region. Similarly, the posterior face has a posterior face lateral margin 60 and a posterior face transverse margin 62.

A pair of spaced apart, opposed, generally parallel side faces 64 and 66 extend between the respective anterior face lateral margins 56 and the posterior face lateral margins 60.

A pair of spaced apart, transverse faces 68 and 70 extend between the respective anterior face transverse margins 58 and the posterior face transverse margins 62. In the embodiment of FIG. 5, the transverse faces 68 and 70 are parallel to each other, but that 18 not necessarily the case. Each transverse face (68, 70) has an anterior platform 72 thereon. When the implant 50 is surgically implanted, the anterior platform 72 with the anterior face 52 generally aligned with the anterior side 26 of the vertebra 22, the anterior platform is in facing relationship with the cortical bone region of the vertebra. The anterior platform 72 is therefore made to be about the same width as the cortical bone region of the vertebra.

Figure 8:
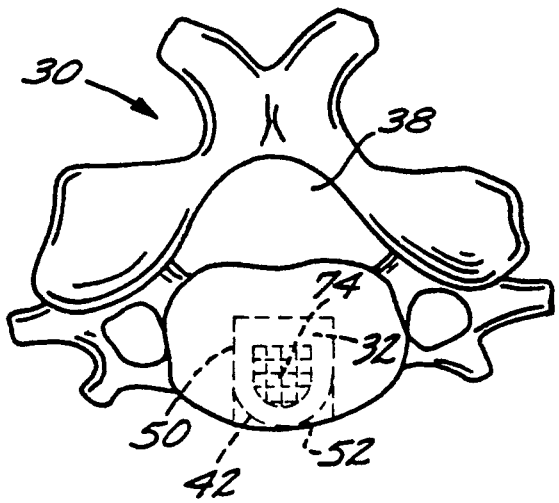
FIG. 8 is a plan view of a cervical vertebra similar to the view of FIG. 2, with the properly positioned spinal disk implant of FIG. 3 indicated in phantom lines.

An engagement region 74 is located on the transverse faces 68, 70 posteriorly of the anterior platform 72. The engagement region 74 has one or more three-dimensional features extending above the general level of the transverse faces 68, 70. In the embodiment of FIGS. 3-5, these three-dimensional features are pyramids 76. After the implant 50 is implanted between two vertebrae 22, as shown in FIG. 8, the pyramidal engagement features contact and engage the cancellous bone of the vertebrae in the central portion 44 of the vertebrae. Since the cancellous bone is softer than the cortical bone, the engagement features sink into the cancellous bone as load is applied and over time after the patient is again carrying weight through the spine. This engagement prevents the implant 50 from shifting its position and moving away from the proper position established by the surgeon.

The implant is made of a ceramic, a metal, a polymer, or a composite material. The implant 50 is desirably made from a material that, after surgical implantation, bonds to the natural bone of the adjacent vertebrae to form a rigid structure. The implant is preferably made from a ceramic, most preferably the ceramic calcium hydroxylapatite, having a chemical formula $Ca10(PO4)6(OH)2$. The use of such materials in implants is known, see for example U.S. Pat. No. 4,863,476, whose disclosure is incorporated by reference. The implant 50 may also be made from a composite material such as the carbon-fiber reinforced plastics disclosed in U.S. Pat. No. 4,904,261, whose disclosure is incorporated by reference. The implant may also be made from a biocompatible orthopedic polymer ("BOP"), such as a copolymer of methylmethacrylate and N-vinylpyrrolidone and calcium gluconate, reinforced with polyamide fibers. Such a material is known in the art, and is described, for example, in G. Lozes et al., "Discectomies of the Lower Cervical spine Using Interbody Biopolymer (BOP) Implants", *Acta Neurochir (Wien)*, vol. 96, pages 88-93 (1989). In some instances, the implant may be made from an uncoated biocompatible metal, such as titanium or a titanium alloy such as Ti-6Al-4V, or a nonreactive metal such as gold. The implant may also be made from such a metal coated with a layer of ceramic or a porous metal coating of sintered beads, mesh, or an amorphous porous layer.

The implant 50 may be made at least in part micro porous, so that it functions as a delivery vehicle for antibiotics or bone stimulating factors such as bone morphogenic protein or osteogenin, which are introduced into the implant before implantation surgery. In the case of the preferred ceramic hydroxylapatite construction of the implant, the density and/or surface morphology of the ceramic can be varied in the sintering process so that it retains the materials to be delivered. The delivery of chemicals by this approach is known in the art, see, for example, H. A. Benghuzzi et al., "The Effects of Density of the Ceramic Delivery Devices on Sustained Release of Androgens in Castrated Rodents," 17th Annual Meeting of the Society for Biomaterials, May 1-5, 1991, page 159.

In another approach, a coated implant is prepared by providing a piece of metal, such as titanium or titanium alloy, in the shape of the implant but slightly undersize in all dimensions. A coating of ceramic, metal, or polymer, of the types described previously, is applied over the piece of metal to enlarge the implant to the proper final dimensions.

Figure 6:
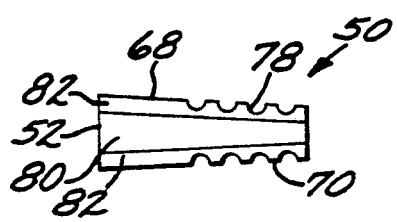
FIG. 6 is a side elevational view of a second form of the spinal disk implant of FIG. 3.

FIG. 6 is an elevational view of another embodiment of the implant 50, having several structural variations from that discussed previously. First, in the embodiment of FIG. 6 the transverse faces 68, 70 are not parallel to each other, but rather are tapered from the anterior end toward the more closely spaced posterior end.

Second, the engagement region 74 has engagement features and are depressions 78 below the general level of the transverse face 68. Third, the engagement region 74 is found on only one of the transverse faces, illustrated as the transverse face 68. Consequently, unlike the symmetrical version of FIG. 5, the embodiment of FIG. 6 is asymmetric about a plane halfway between the transverse faces 68, 70.

Fourth, the embodiment of FIG. 6 has a graded-porosity structure, indicated in the drawing as a dense central region 80 and a less dense, partly porous face region 82. The face region 82 extends about 0.1-0.3 millimeters, preferably about 0.5-0.1 millimeters, from the surface of each transverse face 78, 80. In this embodiment, the entire implant 50 is made of calcium hydroxylapatite ("HA"). The HA in the dense central region 80 has a density of about 95-100 percent of the theoretical density, with very little porosity. The HA in the face region 82 is intentionally somewhat porous, with a density of about 60-95 percent of the theoretical density. The pore sizes in the face region 82 are about 50-500 micrometers in diameter, most preferably about 100-250 micrometers in diameter.

Figure 7:
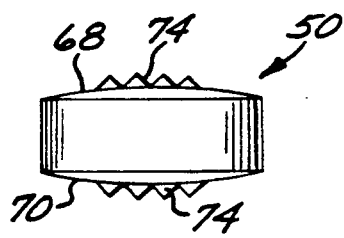
FIG. 7 is a side elevational view of a third form of the spinal disk implant of FIG. 3.

FIG. 7 presents another structural modification to the basic implant 50. In this embodiment, the transverse faces 68, 70 are convexly bowed outwardly. The bowing may be from the anterior end to the posterior end, or from side to side, or both.

Figure 9:
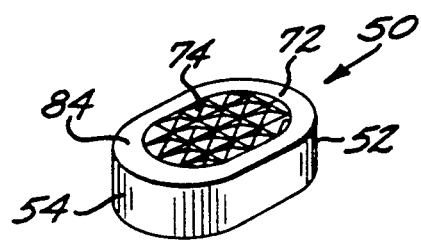
FIG. 9 is a perspective view of a second embodiment of a spinal disk implant.

Another form of spinal disk implant 50 is shown in FIG. 9. This embodiment has a convexly curved posterior face 54, as well as a convexly curved anterior face 52. With the covex curvature on both ends, the implant of FIG. 9 may be made end-to-end symmetric, if desired. If the implant is made end-to-end symmetric, then a posterior platform 84 is provided symmetric with the anterior platform 72. In the design of FIG. 3, a posterior platform 84 is normally present, but is not of any particular width.

FIGS. 6 and 7 present a number of design variations for the implant 50. These variations have been illustrated together for convenience. However, they may be used or not used in any combination that may be convenient and appropriate in a particular circumstance.

Figure 10:
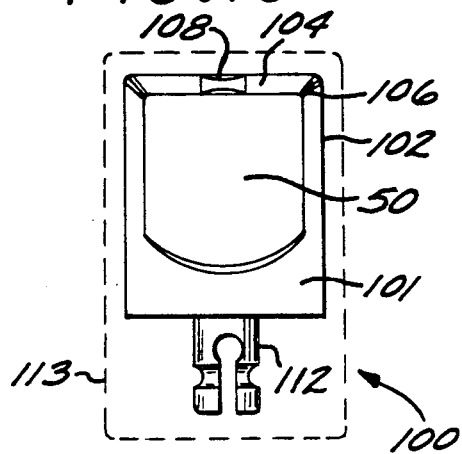
FIG. 10 is a plan view of an implant delivery tool with the disk implant of FIG. 3.
Figure 11:
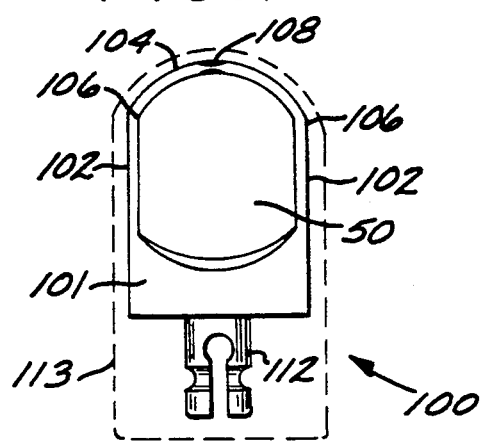
FIG. 11 is a plan view of an implant delivery tool with the disk implant of FIG. 9.
Figure 12:
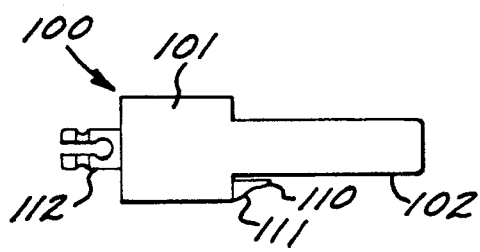
FIG. 12 is an elevational view of one form of the implant tool of FIG. 10.
Figure 13:
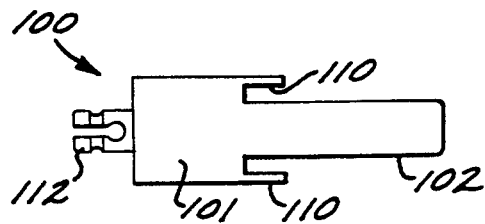
FIG. 13 is an elevational view of another form of the implant tool of FIG. 10.

The invention also extends to an implant delivery tool 100 for use in the surgical operation to implant the implant 50. As illustrated in FIGS. 10-13, the tool 100 has a base 101, and a pair of flexible opposed arms 102 extending from the base 101. The arms 102 are spaced apart and dimensioned to releasably grasp and hold the implant 50 therebetween. FIG. 10 illustrates the configuration of the tool 100 for use in holding the implant 50 pictured in FIG. 3, having only the anterior face curved. FIG. 11 illustrates the configuration of tool 100 for use in holding the implant 50 pictured in FIG. 9, having both the anterior and posterior faces curved. Other configurations could be provided as appropriate.

A release band 104 is fastened to the delivery tool 100 and extends around a portion of the implant 50 to releasably hold it in place on the delivery tool. In the preferred form, the release band 104 extends from the tips 106 of the arms 102 and around the end of the implant 50 to hold it ln place between the arms 102. Equivalently, the release band could extend between other portions of the delivery tool.

A breakable link is provided ln the structure that holds the implant to the delivery tool. The breakable link permits the implant to be controllably released from the delivery tool. In the preferred approach, a breakable weak link 108 is provided in the release band 104, so that the release band 104 can be broken with a slight tug on the tool 100 after the implant is properly positioned between the vertebrae during implantation, leaving the implant at a selected position when the tool is withdrawn. Equivalently, the breakable link could be provided in one of the arms or elsewhere.

It is possible that in some cases the frictional engagement between the implant 50 and the arms 102 will not be sufficient to prevent the implant 50 from tilting or sliding in an end-to-end manner. To prevent such tilting or sliding, a stabilizing lip 110 can extend outwardly from an edge of the base 101. The stabilizing lip, shown in FIG. 12, engages the proximate end of the implant 50 and prevents it from tilting or sliding in an end-to-end fashion. The stabilizing lip 110 may also be provided with an optional stop 111 on its exterior edge that aids the surgeon in positioning the implant during the implantation operation. As the delivery tool 100 is used by the surgeon to insert the implant 50 between two vertebrae, the stop 111 engages the anterior edge of one of the vertebra when the implant has reached the proper position. In a further embodiment shown in FIG. 13, two oppositely disposed stabilizing lips 110 (in this case having no stops 111) are provided to hold the implant 50 even more securely. The stabilizing lips can be tapered to ease their insertion between the vertebral bodies during implant placement.

An engagement tip 112 extends rearwardly from the base 101. This tip 112 engages with a handle, to be described subsequently. The tip may have any appropriate form that cooperates with the handle, as shown in the figures.

The base 101, arms 102, release band 104, weak link 108, engagement tip 112, and stabilizing lip or lips 110 are preferably made of a sterilizable plastic such as item ( ®) available from General Electric Plastics, or Delrin ( ®) available from DuPont. The tool 100 can be made in one piece by injection molding, and is therefore relatively inexpensive and disposable. The release band 104 is a thin ribbon of such plastic, and the weak link 108 is a constricted region of the ribbon that can be easily broken by a tug on the tool 100.

The cooperative design of the implant 50 and the delivery tool 100 is an important feature of the invention. In the past, it has been known in some cases to use a delivery tool that threadably engaged with a threaded bore in the implant. Studies associated with the present invention have demonstrated that a bore, whether threaded or not, in an implant 50, made of a material of relatively low ductility, can significantly weaken the implant 50 even though it is to be used in compression. Avoiding bores and threaded bores in the implant, and provision of an operable delivery tool for this design limitation, adds to the strength and reliability of the implant after implantation.

Figure 14:
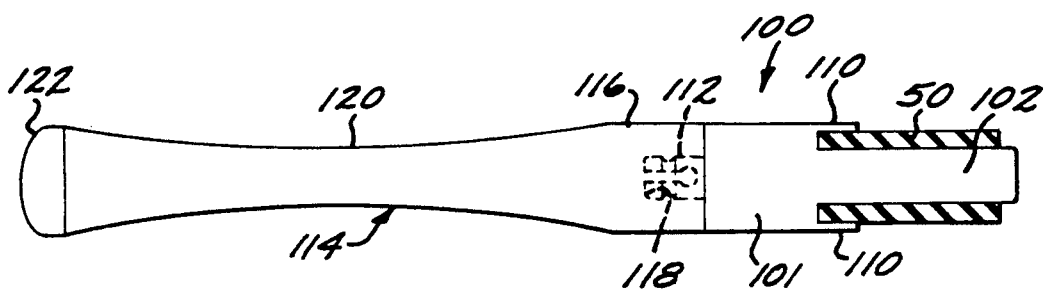
FIG. 14 is a plan view of an implant delivery tool of FIG. 13 and implant of FIG. 10, with attached handle.

FIG. 14 depicts a reusable handle 114 that can be used to place the implant 50 in the desired location during a surgical procedure. The handle 114 has a forward end 116 with a recess 118 therein, dimensioned to firmly but releasably receive the engagement tip 112 of the tool 100. A grip 120 is provided in the intermediate portion of the handle 114, permitting the surgeon to comfortably hold the handle 114 and thence the tool 100 and the implant 50 mounted therein. A butt end 122 of the handle 114 is rounded so that the surgeon may strike it with a surgical hammer if necessary to urge the implant 50 into place between two vertebrae that have been slightly spread apart from their normal spacing during the surgical procedure.

In a preferred embodiment, the delivery tool and implant are furnished together as a kit, for the convenience of the surgeon. The kit allows sterilization of the tool and implant to be readily accomplished either during initial packaging or in the operating room. The kit form also allows the hospital to conveniently stock a range of sizes and configurations of implant that might be needed, giving the surgeon great latitude in the action taken during the procedure, while minimizing the duration of the procedure.

It is preferred to package the delivery tool and implant in a presterilized package, indicated in broken lines as the package 113 in FIGS. 10 and 11. The package may also be furnished so that it and the contents of the package can be sterilized in the operating room, or such that the delivery tool and implant can be removed from the package and sterilized in the operating room. The first approach is preferred, because of its convenience.

To use the kit form of the invention, the required sizes or possible range of implant sizes of the kits are made available in the operating room, preferably in the presterilized package form. During the surgical procedure, the surgeon selects the required implant, and affixes the delivery tool 100 to the handle 114 using the engagement tip 112. The surgeon then uses the handle 114 to manipulate the implant 50 into the proper intervertebral position, tapping the butt end 122 if necessary. When the implant 50 is properly positioned, the vertebrae are allowed to relax slightly back to their normal positions, capturing the implant 50 therebetween. If the surgeon is satisfied with the placement, he or she tugs on the handle 114 to break the weak link 108. The entire delivery tool 100 and handle 114 are withdrawn, and the placement is complete. If, on the other hand, the surgeon is not satisfied, the vertebrae can be tensioned to spread them slightly and to permit removal of the implant. The procedure is repeated with another prepackaged implant and delivery tool available in the operating room.

The present approach provides a spinal disk implant and delivery tool for its implantation. The implant is of a design and material of construction selected to improve the fusion of the adjacent vertebrae, and to permit the implant to be readily implanted. Although particular embodiments of the invention have been described in detail for purposes of illustration, various modifications may be made without departing from the spirit and scope of the invention. Accordingly, the invention is not to be limited except as by the appended claims.

What is claimed is:

1. A spinal disk implant, comprising a solid body having
    a convexly curved anterior face, the anterior face having a curvature of about that of the anterior surface of a human vertebra and having an anterior face lateral margin and a curved anterior face transverse margin;
    a posterior face spaced apart from the anterior face and having a posterior face lateral margin and a posterior face transverse margin;
    a pair of generally parallel, spaced apart, opposed side faces extending between the lateral margins of the anterior face and the posterior face; and
    a pair of spaced apart, opposed transverse faces extending between the transverse margins of the anterior face and the posterior face, each transverse face having an anterior platform and at least one of the transverse faces having an engagement region located posterior of the anterior platform, the engagement region having three-dimensional features thereon raised above the transverse face, a width of the anterior platform being about that of a thickness of anterior cortical bone of a human vertebra, the spinal disk implant being made of a biocompatible synthetic material.

2. The implant of claim 1, wherein the posterior face is convexly curved.

3. The implant of claim 1, wherein the posterior face is flat.

4. The implant of claim 1, wherein the transverse faces are generally parallel.

5. The implant of claim 1, wherein the transverse faces are convexly bowed.

6. The implant of claim 1, wherein the posterior face is convexly curved symmetrically with respect to the anterior face.

7. The implant of claim 6, wherein the solid body is symmetric about a plane lying halfway between the anterior face and the posterior face.

8. The implant of claim 1, wherein both transverse faces have three-dimensional features thereon.

9. The implant of claim 8, wherein the solid body is symmetric about a plane lying halfway between the transverse faces.

10. The implant of claim 9, wherein the transverse faces are parallel to each other.

11. The implant of claim 9, wherein the transverse faces are tapered toward each other.

12. The implant of claim 1, wherein the solid body is formed of a material selected from the group consisting of a ceramic, a metal, a polymer, and a composite material.

13. The implant of claim 1, wherein the solid body is formed of a ceramic.

14. The implant of claim 1, wherein the solid body is formed of caclium phosphate.

15. The implant of claim 1, wherein the solid body is formed of hydroxylapatite.

16. The implant of claim 1, wherein the solid body is formed of a material selected from the group consisting of titanium and a titanium alloy.

17. The implant of claim 1, wherein the solid body is formed of a material that bonds to natural bone.

18. The implant of claim 1, wherein the solid body is formed at least in part of a material that is at least in part microporous.

19. The implant of claim 18, wherein the body has a central dense portion and a microporous coating.

20. A spinal disk implant, comprising a solid body having:
    four faces arranged to define a right-rectangular body, including two opposed side faces and two opposed transverse faces, at least one of the transverse faces having a central region with three-dimensional features thereon raised above the transverse face and an anterior platform region lying along an anterior margin of the transverse face;
    a convexly curved anterior face defining one end of the right-rectangular body; and
    a posterior face defining the other end of the right-rectangular body, the solid body being made of a material selected from the group consisting of a ceramic, a metal, a polymer, and a composite material.

21. The implant of claim 20, further including a posterior platform region lying along a posterior margin of the transverse face.

22. The implant of claim 20, wherein the posterior face is convexly curved.

23. The implant of claim 20, wherein the solid body is symmetric about a plane lying halfway between the anterior face and the posterior face.

24. The implant of claim 20, wherein both transverse faces have three-dimensional features, anterior platforms, and posterior platforms thereon.

25. The implant of claim 20, wherein the solid body is formed of a material selected from the group consisting of a ceramic, a metal, a polymer, and a composite material.

26. The implant of claim 20, wherein the solid body is formed of a ceramic.

27. The implant of claim 20, wherein the solid body is formed of calcium phosphate.

28. The implant of claim 20, wherein the solid body is formed of hydroxylapatite.

29. The implant of claim 20. wherein the solid body formed of a material selected from the group consisting of titanium and a titanium alloy.

30. The implant of claim 20, wherein the solid body is formed of a material that bonds to natural bone.

31. The implant of claim 20, wherein the solid body is formed at least in part of a material that is at least in part microporous.

32. The implant of claim 31, wherein the body has a central dense portion and a microporous coating.

33. A spinal disk implant, comprising a solid body having
a convexly curved anterior face, the anterior face having a curvature of about that of the anterior surface of a human vertebra and having an anterior face lateral margin and a curved anterior face transverse margin;
a posterior face spaced apart from the anterior face and having a posterior face lateral margin and a posterior face transverse margin;
a pair of generally parallel, spaced apart, opposed side faces extending between the lateral margins of the anterior face and the posterior face; and
pair of spaced a part, opposed transverse faces extending between the transverse margins of the anterior face and the posterior face, each transverse face having an anterior platform and at least one of the transverses faces having an engagement region located posterior of the anterior platform, the engagement region having three-dimensional features thereon raised above the transverse face, a width of the anterior platform being about that of a thickness of anterior cortical bone of a human vertebra,
the spinal disk implant being made of a nonmetallic material selected from the group consisting of calcium phosphate and hydroxylapatite.

* * * * *